United States Patent [19]

Herbert et al.

[11] Patent Number: 5,565,484
[45] Date of Patent: Oct. 15, 1996

[54] BENZENESULPHONYLINDOLE DERIVATIVES FOR THE PREPARATION OF MEDICINES

[75] Inventors: Jean-Marc Herbert, Tournefeuille, France; Pierre Chatelain, Brussels, Belgium

[73] Assignee: Sanofi, Paris, France

[21] Appl. No.: 282,288

[22] Filed: Jul. 29, 1994

[30] Foreign Application Priority Data

Jul. 30, 1993 [FR] France ................... 93 09452

[51] Int. Cl.⁶ ................ A61K 31/435; C07D 213/70
[52] U.S. Cl. ................ 514/418; 548/484; 548/486
[58] Field of Search ................ 548/484, 486; 514/418

[56] References Cited

FOREIGN PATENT DOCUMENTS

| | | |
|---|---|---|
| 0302793 | 2/1989 | European Pat. Off. . |
| 0382629 | 8/1989 | European Pat. Off. . |
| 0382628 | 8/1990 | European Pat. Off. . |
| 0382618 | 8/1990 | European Pat. Off. . |
| 576347 | 12/1993 | European Pat. Off. ............... 548/486 |

*Primary Examiner*—Jacqueline Haley
*Attorney, Agent, or Firm*—Jacobson, Price, Holman & Stern, PLLC

[57] ABSTRACT

The invention relates to use of at least one indole derivative of general formula:

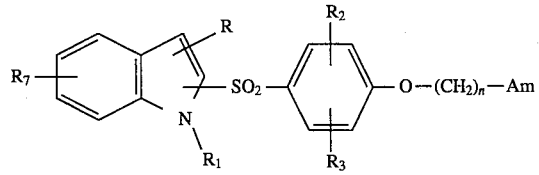

or of one of the pharmaceutically acceptable salts thereof, in which:

Am is selected from radical (a) and (b) defined as follows:

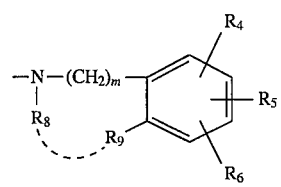

R is a $C_1$–$C_6$ alkyl or $C_3$–$C_6$ cycloalkyl radical $R_1$ represents hydrogen or a $C_1$–$C_4$ alkyl radical $R_2$ and $R_3$, which may be identical or different, represent hydrogen, the methyl or ethyl radical or a halogen $R_4$, $R_5$ and $R_6$, which may be identical or different, represent hydrogen, a $C_1$–$C_4$ alkyl or $C_1$–$C_4$ alkoxy radical or a halogen $R_7$ represents hydrogen or a halogen $R_8$ represents hydrogen or a $C_1$–$C_4$ alkyl radical $R_9$ represents hydrogen or, when $R_8$ and $R_9$ are taken together, form the methylene radical m represents 1 or 2 n represents 2, 3 or 4 for preventing or treating diseases involving a proliferation of smooth muscle cells.

6 Claims, No Drawings

BENZENESULPHONYLINDOLE DERIVATIVES FOR THE PREPARATION OF MEDICINES

The present invention generally relates to a new use of indole derivatives for the preparation of a medicine.

In particular, the invention relates to a new use of benzenesulphonylindole derivatives of general formula:

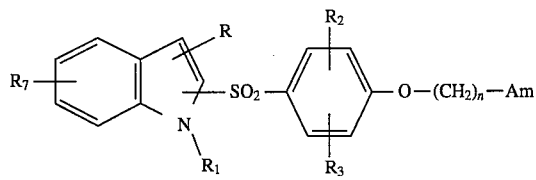

in which:

Am is selected from radical (a) and (b) defined as follows:

 (a)

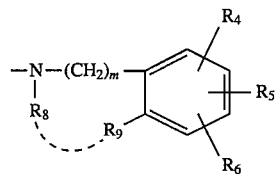 (b)

R is a $C_1$–$C_6$ alkyl or $C_3$–$C_6$ cycloalkyl radical $R_1$ represents hydrogen or a $C_1$–$C_4$ alkyl radical $R_2$ and $R_3$, which may be identical or different, represent hydrogen, the methyl or ethyl radical or a halogen $R_4$, $R_5$ and $R_6$, which may be identical or different, represent hydrogen, a $C_1$–$C_4$ alkyl or $C_1$–$C_4$ alkoxy radical or a halogen $R_7$ represents hydrogen or a halogen $R_8$ represents hydrogen or a $C_1$–$C_4$ alkyl radical $R_9$ represents hydrogen or, when $R_8$ and $R_9$ are taken together, form the methylene radical m represents 1 or 2 n represents 2, 3 or 4 and the pharmaceutically acceptable salts thereof, for the preparation of a medicine.

Thus, taking the above values into account:

R may in particular represent a methyl, ethyl, n-propyl, isopropyl, n-butyl, n-pentyl, n-hexyl or cyclopropyl radical, $R_1$ may in particular represent the methyl radical, $R_2$ and $R_3$ may in particular represent chlorine or bromine, $R_4$, $R_5$ and $R_6$ may in particular represent the methyl or methoxy radical or chlorine, $R_7$ may in particular represent chlorine, $R_8$ may in particular represent the methyl radical.

One particular class of compounds of formula I is represented by those in which R represents the isopropyl or cyclopropyl radical and $R_2$ and $R_3$, which are identical, represent hydrogen.

Another class of compounds of formula I is represented by these compounds in which $R_7$ represents hydrogen, on the one hand, and one of $R_4$, $R_5$ and $R_6$ represents hydrogen or the methyl or methoxyradical, the other two representing the methyl or methoxy radical, on the other hand.

Another class of compounds of formula I is formed by these compounds in which the substituted alkoxybenzenesulphonyl chain is found in the 2-position of the indole ring and in particular represents the 4-{3-[N-methyl-N-( 3,4-dimethoxyphenethyl)amino]propoxy}benzenesulphonyl group.

Examples of pharmaceutically acceptable salts of the compounds of formula I which may be mentioned are salts formed from an organic acid such as the oxalate, maleate, fumarate, methenesulphonate, benzoate, ascorbate, pamoate, succinate, hexamate, bismethylene-salicylate, ethanedisulphonate, acetate, propionate, tartrate, salicylate, citrate, gluconate, lactate, malate, cinnamate, mandelate, citraconate, aspartate, palmitate, stearate, itaconate, glycolate, p-amino-benzoate, glutamate, benzenesulphonate and theophylline-acetate salts and the salts formed from an amino acid such as the lysine or histidine salts, or alternatively salts formed from an inorganic acid such as the hydrochloride, hydrobromide, sulphate, sulphamate, phosphate and nitrate salts.

In the last two decades, very specific interest has been paid to the role played by the proliferation of smooth muscle cells of the intima in the development of atherosclerosis.

The characterization of experimental lesions induced in animals and the histological study of lesions occurring in human coronary arteries have demonstrated that an atherosclerotic plaque starts as a nodular proliferation of smooth muscle cells, which subsequently becomes complicated by the accumulation of spumous cells filled with lipids, of necrotic cells and of calcification.

These discoveries suggest that agents interfering with the proliferation of smooth muscle cells may be of therapeutic value in the prevention and treatment of atherosclerosis.

Calcium antagonists constitute one group of pharmacologically active agents which inhibit the $C^{++}$-ion-dependent processes. Their main mechanism of action is established by blocking the entry of calcium ions into the cells. Clinically, calcium antagonists have proved efficient in the treatment of angina, hypertension and cardiac arrhythmia.

It has been widely reported in the scientific literature that anticalcium agents selectively inhibit the proliferation of smooth muscle cells occurring after an experimental lesion. These calcium antagonists, by this mechanism, will consequently provide a beneficial effect in the prevention and treatment of atherosclerosis.

Among the $C^{++}$-antagonist agents which have been studied as inhibitors of the proliferation of smooth muscle cells, there may be mentioned nifedipine, diltiazem or verapamil. The latter is characterized by the presence of an N-methyl-N-(3,4-dimethoxyphenethyl)amino chain in its molecule, as well as other anticalcium agents which are described in Patent Applications EP-A-0,302,793, 0,382,618, 0,382,628 and 0,382,629, in particular 3-isopropyl-1-[4-{3-[N-methyl-N-(3,4-dimethoxyphenethyl)amino]propoxy}benzenesulphonyl]-indolizine or fantofarone.

It has now surprisingly been found that indole derivatives containing such an N-methyl-N-(3,4-dimethoxyphenethyl)amino chain, and more generally the indole derivatives of formula I, which form the subject of the abovementioned patent applications, and the pharmaceutically acceptable salts thereof, are endowed with remarkable biochemical and pharmacological properties with respect to the vascular wall. Indeed, these compounds have proved capable of inhibiting the proliferation of smooth muscle cells such as, for example, aortic, mesenteric, femoral or carotid arterial cells.

On the other hand, verapamil and fantofarone, under the experimental conditions studied, have generally revealed themselves to be devoid of such properties or have shown themselves to be endowed with these properties at high, or even subtoxic, doses.

The compounds of formula I and the pharmaceutically acceptable salts thereof, as well as the pharmaceutical or veterinary compositions containing them, will consequently be useful for the purpose of preventing or treating, for example, restenosis after coronary transluminal angioplasty or atherosalerosis, in which the proliferation of vascular smooth muscle cells has been described as an important pathogenic event.

Consequently, a first subject of the invention relates to the use of at least one indole derivative of formula I or of one of the pharmaceutically acceptable salts thereof, for the preparation of a medicine intended for preventing or treating diseases involving a proliferation of smooth muscle cells.

By way of example of compounds which are useful in this new use, there may be mentioned the indole derivatives of formula I below, which have been described in the above-mentioned patents:

1-Methyl-3-isopropyl-2-[4-{3-[N-methyl-N-(3,4-dimethoxyphenethyl)amino]propoxy}benzenesulphonyl]indole hydrogen oxalate (SR 33805 A)

1-Methyl-2-{4-[3-(6,7-dimethoxy-1,2,3,4-tetrahydro-N-isoquinol- 2-yl)propoxy]benzenesulphonyl}-3-isopropyl-indole hydrogen fumarate (SR 33905 A)

1-Methyl-3-isopropyl-2-[4-{3-[N-methyl-N-(3,4,5-trimethoxyphenethyl)amino]propoxy}benzenesulphonyl]indole hydrochloride (SR 34041 A)

1-Methyl-3-isopropyl-2-[4-{3-[N-(3,4,5-trimethylphenethyl)amino]propoxy}benzenesulphonyl] indole hydrochloride (SR 34079 A).

Among the compounds of formula I, 1-methyl -3-isopropyl- 2-[4-{3-[N-methyl-N-(3,4-dimethoxyphenethyl)amino] propoxy}benzenesulphonyl] indole, referred to below as SR 33805, of formula:

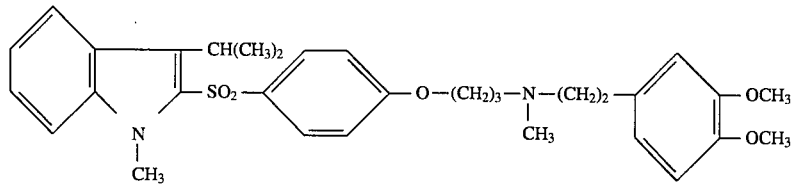

and the pharmaceutically acceptable salts thereof, has shown the most interesting inhibitory potentiality with respect to the proliferation of smooth muscle cells. In this connection, SR 33805 and the pharmaceutically acceptable salts thereof constitute preferred compounds according to the invention.

SR 33805 in its hydrogen oxalate form has been specifically described in Patent Application EP-A- 0,302,793, whereas no other salt of this compound was either cited or given as example therein.

However, it is recognized that the oxalate anion does not constitute the counterion of first choice for the formation of pharmaceutically acceptable salts.

Now, it has been found that the methanesulphonate of SR 33805, referred to below as SR 33805 C, constitutes a particularly advantageous compound on account of a set of criteria which impart essential qualities to it for use in the preparation of a medicine, more generally for a pharmaceutical or veterinary composition.

For example, contrary to the other salts of SR 33805, the methanesulphonate of this compound, given its good aqueous solubility, proved much more suitable for the production of injectable solutions, #or example 5% injectable solutions or even lower concentrations.

Solubility tests carried out with SR 33805 C, SR 33805 A (SR 33805$^{acid\ oxalate}$) and SR 33805 B (SR 33805 fumarate) revealed the degrees of solubility below:

| Results | (1) | (2) | (3) |
|---|---|---|---|
| SR 33805 A | 0.007% | 0.019% | 0.031% |
| SR 33805 B | 0.015% | 0.010% | 0.026% |
| SR 33805 C | 6.75% | 7.99% | 9.83% |

(1) solubility in water at 25° C. after stirring for 72 hours
(2) solubility in water of pH = 3.6
(3) solubility after addition of the product to be tested to water at 70° C., stirring and continuation of stirring for 72 h at 25° C.

Similarly, SR 33805 C shows no signs of hygroscopicity, has good stability under various storage conditions and may be obtained in a crystalline form which is compatible with use for the preparation of pharmaceutical or veterinary forms, contrary to other salts of SR 33805, which proved very much inferior by these criteria.

Consequently, another subject of the invention relates to the methanesulphonate of SR 33805 as a new product.

Similarly, the invention relates to a medicine which is essentially a pharmaceutical or veterinary composition containing as active principle SR 33805 methanesulphonate in combination with a pharmaceutical vehicle or a suitable excipient.

For the reasons outlined above. SR 33805 methanesulphonate constitutes a particularly preferred compound according to the invention.

Further, another indole derivative proved to be very useful on account of its strong activity as inhibitor of the proliferation of smooth muscle cells and its very moderate or lack of activity on the cardiovascular system, namely 1-methyl-3-isopropyl-2-{4-[3-(N-methylamino)propoxy]benzenesulfonyl} indole, referred to below as SR 34549.

Indeed this compound appeared to be devoid of inhibitory properties of the calcium translocation when tested in vitro.

Hence, the invention also relates to SR 34549 and more generally to new indole derivatives of formula I in which Am represents —NHR$_8$, and the pharmaceutically acceptable salts thereof The inhibitory properties of the compounds of formula I and of the pharmaceutically acceptable salts thereof with respect to the proliferation of smooth muscle cells have been demonstrated using various biochemical and pharmacological tests, which are summarized below.

I. "in vitro" tests

"in vitro" tests were carried out using human aortic smooth muscle cells at rest ($10^3$ cells per test).

These cells were incubated in the presence of minimum eagle medium to which 5% of an agent inducing a cell proliferation was added. These tests were performed with various increasing doses of the compound to be studied compared with controls.

After incubation for 3 days, the cell growth was stopped by addition of trypsin and the results were expressed as concentrations allowing the cell proliferation to be inhibited by 50% (IC$_{50}$).

The following results were recorded compared with fantofarone, verapamil or nifedipine.

a) Inducing agent: fetal calf serum

| Compound studied | IC$_{50}$ (μM) |
| --- | --- |
| SR 33805 C | 0.9 |
| Fantofarone | 5.5 |
| Verapamil | 10.0 |

Analogous tests performed with other compounds of formula I in the form of pharmaceutically acceptable salts revealed IC$_{50}$s between 0.09 and 3 μM.

b) Inducing agent: foetal growth factor

| Compound studied | IC$_{50}$ (μM) |
| --- | --- |
| SR 33805 C | 0.6 |
| Fantofarone | 2.0 |
| Nifedipine | 1.0 | c) Inducing agent: platelet derived growth factor

| Compound studied | IC$_{50}$ (μM) |
| --- | --- |
| SR 33805 C | 0.3 |
| Fantofarone | >10.0 |
| Nifedipine | >10.0 |

II. "in vivo" tests

1) Inhibition of the Ca$^{++}$ surcharge after treatment with vitamin D$_3$ in rats A test was performed on rats, to which 300,000 IU/kg of vitamin D$_3$ were administered intramuscularly, followed by oral administration of a daily dose of the compound to be studied. The oral treatment using the compound to be tested was continued for 3 days, the animals were sacrificed and the Ca$^{++}$ was then assayed in various arterial regions (femoral, mesenteric, aortic etc.).

In this test, SR 33805 C exerts, from the dose of 2 mg/kg administered twice daily, a significant effect of inhibition of the Ca$^{++}$ surcharge in the aorta. An analogous significant effect was recorded in the mesenteric artery from the dose of 5 mg/kg administered twice daily.

By way of comparison, fantofarone tested under the same experimental conditions induced a significant decrease in the total Ca" content from 100 mg/kg administered twice daily. SR 33805 C was thus revealed in this test to be 20 to 50 times more active than fantofarone. Under the same experimental conditions, verapamil showed itself to be 15 to 30 times less active than SR 33805 C.

2) Inhibition of myointimal proliferation induced in rabbit carotid arteries after lesion of the endothelium For this purpose, rabbits from which the endothelium of the carotid artery was removed were used.

Two hours before the lesion, the compound to be studied was administered orally. The treatment was continued orally, daily for 16 days, and the surface areas of the intima and of the media were then determined by morphometric measurement.

The results showed that after treatment for 16 days from the dose of 1.5 mg/kg, SR 33805 C significantly inhibits (–58%) myointimal proliferation.

At the maximum doses tested, nifedipine (6 mg/kg or twice 6 mg/kg), fantofarone (12 mg/kg), verapamil (twice 6 mg/kg) or diltiazem (twice 6 mg/kg) exhibited no significant effect on myointimal hyperplasia.

These various results show that the indole derivatives of formula I and the pharmaceutically acceptable salts thereof, particularly SR 33805 in its methanesulphonate form, are revealed as being far superior to other anticalcium agents, namely verapamil, fantofarone or nifedipine, as inhibitors of the proliferation of smooth muscle cells.

The indole derivatives of formula I and the pharmaceutically acceptable salts thereof my be prepared as described in the abovementioned patent applications.

For example, these compounds may be prepared by treating a 4-hydroxybenzenesulphonyl derivative of general formula:

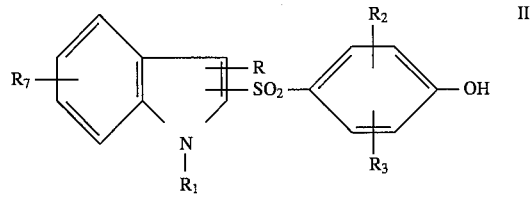

in which R, R$_1$, R$_2$, R$_3$ and R$_7$ have the same meaning as above, with a halide of general formula:

or

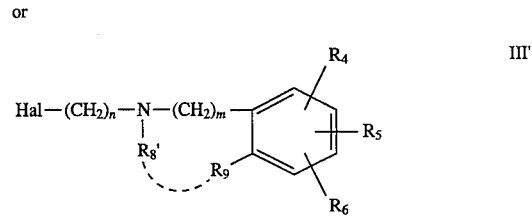

in which R$_4$, R$_5$, R$_6$, R$_8$, R$_9$, m and n have the same meaning as above Hal represents halogen preferably bromine R$_8$ represents (C$_1$–C$_4$) alkyl and Z represents a protective group such as terbutoxycarbonyl (BOC), the reaction being carried out in the presence of a basic agent such as an alkali metal carbonate, an alkali metal hydroxide, an alkali metal hydride or an alkali metal alkoxide in order to obtain:

either the compounds of formula I in which Am is a (b) radical, or N-protected compounds which are subsequently treated by trifluoroacetic acid in order to obtain the compounds of formula I in which Am is radical (a) which compounds of formula I may, if so desired, be reacted with a suitable acid in order to form a pharmaceutically acceptable salt of this compound. Alternatively, the compounds of formula I may be prepared by reacting an indole derivative of formula II with a dihaloalkane of general formula

in which Hal and n have the same meaning as above, the reaction being carried out in a solvent such as methylethylketone or N,N-dimethylformamide in the presence of a basic agent such as an alkali metal carbonate, an alkali metal hydride, an alkali metal hydroxide or an alkali metal alkoxide in order to obtain an haloalkoxy-benzenesulfonyl-indole derivative.

The obtained haloalkoxybenzenesulfonyl-indole derivative is then reacted with an amine of general formula

in which Am has the same meaning as above, the reaction being carried out in a polar or non polar solvent and in the presence of an acid scavenger or in the presence of an excess of the amine of formula V, in order to obtain the compounds of formula I which may, if so desired, be reacted with a suitable acid in order to form a pharmaceutically acceptable salt of this compound.

The medicine according to the invention, when it consists of a pharmaceutical or veterinary composition, may itself also be prepared in a known manner as described in the abovementioned patent applications, essentially by combination of at least one indole derivative of formula I or of one of the pharmaceutically acceptable salts thereof with a pharmaceutical vehicle or a suitable excipient.

Finally, the indole derivatives of formula I and the pharmaceutically acceptable salts thereof my be used for therapeutic purposes in similar doses to those recommended in the abovementioned patent applications, which, for a human being of 60 kg, are generally at daily doses ranging from 2 to 800 mg depending on the route of administration chosen.

The non-limiting example which follow illustrate the preparation of SR 33805 C and of a pharmaceutical composition containing it:

EXAMPLE 1

Preparation of 1-methyl-3-isopropyl-2-[4-{3-[N-methyl-N-(3,4-dimethoxyphenethyl)amino] propoxy}benzenesulphonyl]-indole methanesulphonate To a mixture of 9.9 g (0.003 mol) of 2-(4-hydroxybenzenesulphonyl)- 3-isopropyl-1-methylindole in 165 ml of N,N-dimethylformamide are added 29 g (0.21 mol) of anhydrous and finely ground potassium carbonate. The mixture is stirred for 0.5 hour and 13.3 g (0.033 mol) of 90% 1-chloro-3-[N-methyl-N-(3,4-dimethoxylphenethyl)amino] propyl hydrogen oxalate are added.

The mixture is heated at 100° C. for 1 hour and is allowed to return to room temperature with stirring. 450 ml of water and ice are poured in and the mixture is stirred for 0.25 hour. It is extracted with three times 150 ml of diethyl ether, washed twice with 150 ml of water and dried over sodium sulphate.

3.5 g of methanesulphonic acid dissolved in 50 ml of ethyl ether are added to the ether solution obtained and it is left to crystallize for 24 hours. It is drained, washed with ethyl ether and dried under vacuum at 50 ° C.

In this way, 1-methyl-3-isopropyl-2-[4-{3- [N-methyl-N-( 3,4-dimethoxylphenethyl)amino]propoxy}benzene-sulphonyl]indole methanesulphonate is obtained in the form of a crystalline white solid.

M.p.: 166° C. (¾ ethyl acetate/isopropanol).

EXAMPLE 2

Preparation of 1-methyl-3-isopropyl-2-{4-[3-(N-methylamino)propoxy]benzenesulfonyl} indole hydrochloride:

5.5 g (0.0145 mol) of 1-methyl-3-isopropyl-2-[4-(3-bromopropoxy)benzenesulfonyl] indole are dissolved in 70 ml of N,N-dimethylformamide and then the reaction mixture is cooled at 0° C. Next 6.7 ml of a 3% solution of methylamine in methanol are added and the reaction mixture is left at room temperature for 12 to 14 hours. The reaction mixture is poured into water, extracted with diethyl ether and the hydrochloride salt is formed upon addition of hydrochloric acid in diethyl ether. Recrystallization is carried out in ethyl acetate.

In this way, 2.8 g of 1-methyl-3-isopropyl-2-{4-[3-(N-methylamino)propoxy]benzenesulfonyl} indole hydrochloride are obtained.

Yield: 44.2% M.p: 127° C. (ethyl acetate)

EXAMPLE 3

Preparation of 3-isopropyl-2-{4-[3-(N-methylamino) propoxy]benzenesulfonyl}-indole oxalate:

3.15 g (0.01 mol) of 3-isopropyl-2-{4-hydroxybenzenesulfonyl}-indole are dissolved in 20 ml of dimethylsulfoxide and 2.5 g of crushed sodium carbonate are added. The reaction mixture is stirred and 3.1 g (0,015 mol) of N-BOC-N-methyl- 3-aminopropyl chloride are added. The mixture is kept at room temperature for 12 to 14 hours and subsequently heated at 65°–70° C. for 5 hours. The reaction mixture is poured into water, extracted with ethyl acetate and the organic phase is washed twice with water. After drying over anhydrous sodium sulfate, filtration and evaporation of the solvent, 5.8 g of an oily residue are obtained. The residue is taken up in 50 ml of dichloromethane and 20 ml of trifluoroacetic acid and the mixture is stirred at room temperature for one hour. The mixture is then evaporated to dryness (bath temperature: 50° C.) and the residue is taken up in water. A solution of sodium hydroxide is added, the mixture is extracted with diethyl ether and the organic phase is washed with water. After drying and evaporation of the solvent, 1.26 g of a residue are obtained and purified by chromatography on a silica gel column using methanol as eluant. 0.560 g of the desired product in a basic form are obtained. the oxalate salt being prepared upon addition of oxalic acid in diethyl ether. In this way 3-isopropyl-2-{4-[3-(N-methylamino)propoxy]benzenesulfonyl}-indole is provided.

Yield: 14.5% M.p: 115° C. (isopropanol)

Using the same methods as described above, 3-isopropyl-2-{4-{3-[N-(3,4-dimethoxyphenethyl)amino] propoxy}benzene-sulfonyl}-indole (example 4) is prepared. M.p: 205° C. (ethyl acetate)

EXAMPLE 5

Gelatin capsules of the following composition were prepared according to known pharmaceutical techniques:

| Ingredients | Mg |
|---|---|
| SR 33805 C | 50 |
| Lactose | 25 |
| Magnesium stearate | 25 |
| | 100 |

We claim:
1. 1-methyl-3-isopropyl-2-[4-(3-[N-methyl-N-(3,4-dimethoxyphenethyl)amino]propoxy)benzenesulphonyl]indole methanesulphonate.

2. A pharmaceutical or veterinary composition comprising a pharmaceutically effective amount of 1-methyl-3-isopropyl- 2-[ 4-{ 3-[N-methyl-N-(3,4-dimethoxyphenethyl)amino]propoxy} benzenesulphonyl] indolemethanesulphonate, in combination with a pharmaceutical vehicle or excipient.

3. 1-methyl-3-isopropyl-2-[4-{3-(N-methylamino) propoxy)benzenesulphonyl]indole or a pharmaceutically acceptable salt thereof.

4. A process for preventing or treating a disease involving a proliferation of smooth muscle cells selected from restenosis after coronary transluminal angioplasty and atherosclerosis comprising administering to a human a compound selected from 1-methyl-3-isopropyl-2-[ 4-(3-[N-methyl-N-(3,4-dimethoxyphenethyl)amino]propoxy)benzenesulphonyl]indole and a pharmaceutically acceptable salt thereof.

5. A process for preventing or treating a disease involving a proliferation of smooth muscle cells selected from restenosis after coronary transluminal angioplasty and atherosclerosis comprising administering to a human 1-methyl-3-isopropyl-2-[4-(3-[N-methyl-N-(3,4-dimethoxyphenethyl)amino]propoxy)benzenesulphonyl]indolemethanesulphonate.

6. A process for preventing or treating a disease involving a proliferation of smooth muscle cells selected from restenosis after coronary transluminal angioplasty and atherosclerosis comprising administering to a human a compound selected from 1-methyl-3-isopropyl-2-[4-(3-(N-methylamino)-propoxy}benzenesulphonyl]indole and a pharmaceutically acceptable salt thereof.

* * * * *